United States Patent [19]
Pan

[11] Patent Number: 6,052,427
[45] Date of Patent: Apr. 18, 2000

[54] MULTIDIMENSIONAL INTERPOLATION

[75] Inventor: Xiaochuan Pan, Chicago, Ill.

[73] Assignee: ARCH Development Corp., Chicago, Ill.

[21] Appl. No.: 09/166,041

[22] Filed: Oct. 5, 1998

[51] Int. Cl.$^7$ .................................................. A61B 6/03
[52] U.S. Cl. ................................ 378/4; 378/15; 378/901
[58] Field of Search .............................. 378/4, 8, 15, 62, 378/901

[56] References Cited

U.S. PATENT DOCUMENTS

| | | | |
|---|---|---|---|
| 3,862,404 | 1/1975 | Fiedrich | 708/290 |
| 5,175,701 | 12/1992 | Newman et al. | 708/290 |
| 5,469,222 | 11/1995 | Sprague | 348/580 |
| 5,678,033 | 10/1997 | Moledina et al. | 345/502 |

OTHER PUBLICATIONS

Arenson, Jerry, *Data Collection Strategies: Gantries and Detectors,* (Hackensack, New Jersey: Elscint Inc., [no date]).

Barrett, Harrison H., *The Radon Transform and its Applications,* Progress in Optics XXI:218–286 (Elsevier Science Publishers B.V., 1984).

Budinger, Thomas F., *Single Photon Emission Computed Tomography,* ([no date]).

Defrise, Michel, et al., *Exact and Approximate Rebinning Algorithms for 3–D PET Data,* 16:2 IEEE Transactions on Medical Imaging 145–158 (Apr. 1997).

Dreike, Philip, et al., *Convolution Reconstruction of Fan Beam Projections,* 5 Computer Graphics and Image Processing 459–469 (Academic Press, Inc., 1976).

Gullberg, Grant T., et al., *Reconstruction Algorithm for Fan Beam with a Displaced Center–of–Rotation,* MI–5:1 IEEE Transactions on Medical Imaging 23–29 (Mar. 1986).

Gullberg, Grant T., *The Reconstruction of Fan–Beam Data by Filtering the Back–Projection* 10 Computer Graphics and Image Processing 30–47 (1979).

Horn, Berthold K.P., *Fan–Beam Reconstruction Methods,* 67:12 Proceedings of the IEEE 1616–1623 (Dec. 1979).

Jerri, Abdul J., *The Shannon Sampling Theorem—Its Various Extensions and Applications: A Tutorial Review,* 65:11 Proceedings of the IEEE 1565–1596 (Nov. 1977).

Joseph, Peter M., *Overview of the History and Principles of CT Scanning* (University of Pennsylvania, Dept. of Radiology, [no date]).

Kalender, Willi A., et al., *Spiral CT: Medical Use and Potential Industrial Applications,* 3149 Proceedings of SPIE 188–202 (Jul. 1997).

(List continued on next page.)

*Primary Examiner*—David V. Bruce
*Attorney, Agent, or Firm*—Welsh & Katz, Ltd.

[57] ABSTRACT

A method and apparatus are provided for interpolating a first set of multi-dimensional sample values from a second set of multi-dimensional sample values. The method includes the steps of determining a set of relationships between a second sampling space from which the second set of samples are obtained and a first sampling space into which the first set of samples are interpolated and calculating a partial Fourier transform of the second set of samples. The method further includes the steps of obtaining a partial Fourier transform of the first set of samples using the calculated partial Fourier transform of the second set of samples based upon the determined relationship between the first and second space and performing an inverse partial Fourier transform on the obtained partial Fourier transform of the first set of sample values to recover the first set of sample values.

24 Claims, 2 Drawing Sheets

OTHER PUBLICATIONS

Kijewski, Marie Foley, et al., *The noise power spectrum of CT images,* 32:5 Phys.Med.Biol. 565–575 (1987).

Metz, Charles E., et al., *A Unifed Analysis of Exact Methods of Inverting the 2–D Exponential Radon Transform, with Implications for Noise Control in SPECT,* 14:4 IEEE Transactions on Medical Imaging 643–658 (1995).

Meyer, Craig H., et al., *Fast Spiral Coronary Artery Imaging,* 28 Magnetic Resonance in Medicine 202–213 (1992).

Mueller, Rolf K., et al., *Reconstructive Tomography and Applications to Ultransonics,* 67:4 Proceedings of the IEEE 567–586 (Apr. 1979).

Parker, Dennis L., *Optimal short scan convolution reconstruction for fanbeam CT,* 9:2 Med. Phys. 254–257 (Mar./Apr. 1982).

Riederer, Stephen J., et al., *The Noise Power Spectrum in Computed X–ray Tomography,* 23:3 Phys.Med.Biol. 446–454 (1978).

Vannier, M.W., et al., *Principles of Spiral CT,* ([no date]).

You, Hangsheng, et al., *Benefits of Angular Expression to Reconstruction Algorithms for Collimators with Spatially Varying Focal Lengths,* 16:5 IEEE Transactions on Medical Imaging 527–531 (Oct. 1997).

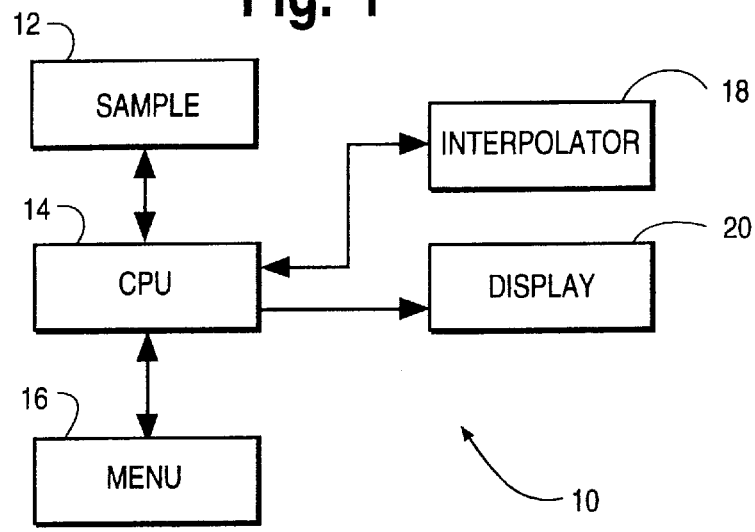
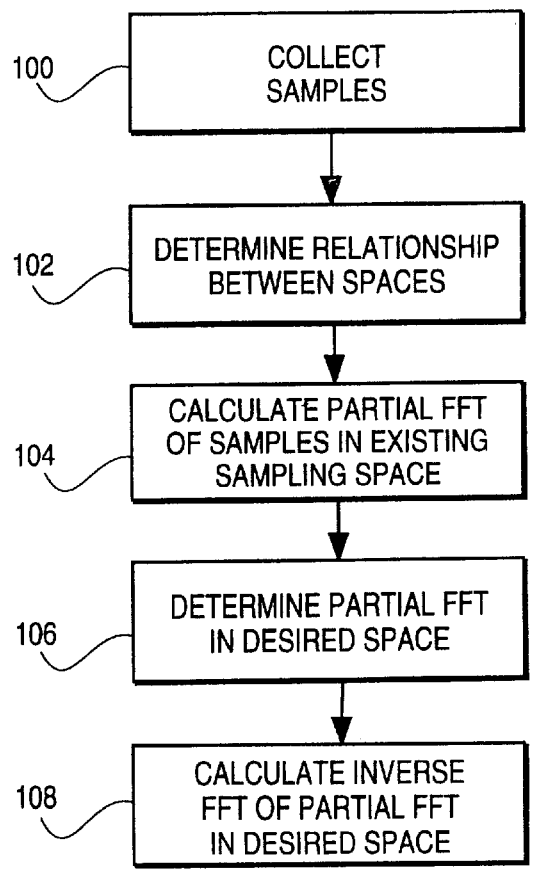

MULTIDIMENSIONAL INTERPOLATION

The U.S. Government has a paid-up license in this invention and the right in limited circumstances to require the patent owner to license others on reasonable terms as provided for by the terms of Grant #CA70449 as awarded by the National Institute of Health.

FIELD OF THE INVENTION

The invention belongs to the field of digital signal processing, which relates to the processing of information by digital computers. Digital signal processing is extensively utilized in electrical engineering and other fields of applied science. In particular, the invention is related to the tomographic reconstruction of medical imaging.

BACKGROUND OF THE INVENTION

In engineering or/and scientific experiments and applications, one acquires a finite set of samples of the underlying multi-dimensional function of interest. However, because of various physical restrictions of the sampling system, these samples are often obtained on nonuniform grids, thereby preventing the direct use and meaningful interpretation of these data. For example, in medical tomographic imaging such as the two-dimensional (2D) fan-beam computed tomography (CT), single-photon emission computed tomography (SPECT), positron emission tomography (PET), spiral (or helical) CT, diffraction tomography (DT), and magnetic resonance imaging (MRI), the acquired data are often sampled on nonuniform grids in the sinogram space, thus preventing the direct use of existing methods that are computationally efficient and numerically stable for reconstruction of tomographic images. In these situations, one can always use various multi-dimensional interpolation (MDI) methods to convert the samples that lie on nonuniform grids into samples that lie on uniform grids so that they can be processed directly and be presented meaningfully.

A wide variety of MDI methods have previously been developed. However, only the methods that are based upon the Whittaker-Shannon sampling (WST) theorem can potentially provide accurate interpolation results. Unfortunately, these methods generally possesses the shortcoming of a great computational burden, which increases drastically as the number of interpolation dimensions increases ("the curse of the dimensionality"). In attempts to alleviate the computational burden, efforts have been devoted previously to developing efficient interpolation methods. However, these methods are all associated with certain approximations. Virtually all of the MDI methods developed previously calculate the desired uniform samples directly from the measured nonuniform samples, which requires the use of computationally burdensome algorithms if accuracy is to be preserved.

Accordingly, a need exists for a computationally more efficient means for multi-dimensional interpolation. More importantly, none of the previously developed multi-dimensional interpolation methods can be applied to certain multi-dimensional problems such as the one that arises in SPECT.

Accordingly, there is a need to develop a computationally efficient method that can accomplish the multi-dimensional interpolation tasks, for which the existing methods are not applicable.

SUMMARY

A method and apparatus are provided for interpolating a first set of multi-dimensional sample values from a second set of multi-dimensional sample values. The method includes the steps of determining a set of relationships between a second sampling space from which the second set of samples are obtained and a first sampling space into which the first set of samples are interpolated and calculating a partial Fourier transform of the second set of samples. The method further includes the steps of obtaining a partial Fourier transform of the first set of samples using the calculated partial Fourier transform of the second set of samples based upon the determined relationship between the first and second space and performing an inverse partial Fourier transform on the obtained partial Fourier transform of the first set of sample values to recover the first set of sample values.

BRIEF DESCRIPTION OF THE DRAWINGS

FIG 1 is a block diagram of an imaging system using the multidimensional interpolation system in accordance with an embodiment of the invention; and FIG. 2 is a flow chart of the interpolation method of the system of FIG. 1;

DETAILED DESCRIPTION OF A PREFERRED EMBODIMENT

Figure 3A:
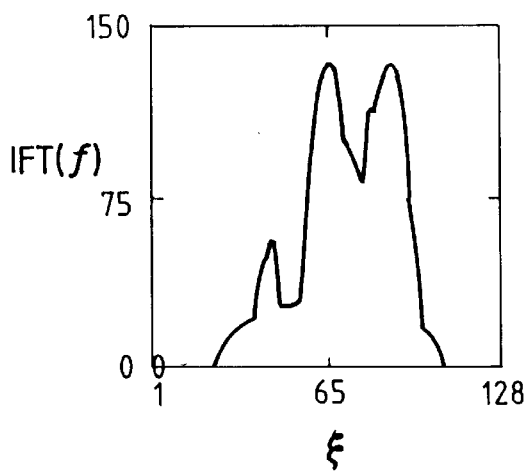
FIG. 3 depicts results of data interpolated on a 128×128 and 128×16 grids, respectively.

FIG. 1 is a multidimensional interpolator 10, generally, in accordance with an illustrated embodiment of the invention. FIG. 2 is a flow chart of processing steps that may be used by the structure of FIG. 1 to interpolate between sampling spaces. Reference may be made to FIGS. 1 and 2 as appropriate to an understanding of the invention.

Under the embodiment, a sampling device 12 acquires samples 100 under an appropriate format (e.g., fan-beam CT, spiral CT, etc.) under the control of a central processing unit (CPU) 14. The CPU 14 may store the samples in a memory unit 16 or processing the samples directly.

Once collected, the samples may be transferred to an interpolator 18. Within the interpolator 18, the samples may be interpolated from a second sampling format (e.g., fan-beam CT) into a first sampling format (e.g., parallel ray CT) under the control of the CPU 14. Once converted the samples may be displayed under a conventional format on a display 20.

In general, conventional interpolation techniques calculate a function by directly using its measured samples. However, because the values of a function can readily be calculated from its Fourier transform (FT), the interpolation task could be compared to estimating the FT of a function from its measured samples. Based upon this observation, an approach is provided for reducing the interpolation dimensions in MDI problems.

Let $f(\vec{x}_1, \vec{x}_2)$ and $g(\vec{y}_1, \vec{y}_2)$ be K-dimensional (KD) band-limited functions, where $\vec{x}_1=(x_1, x_2 \ldots x_k)^T$ and $\vec{y}_1=(y_1, y_2 \ldots y_k)^T$ are kD vectors, $\vec{x}_2=(x_{k+1}, x_{k+2} \ldots x_K)^T$ and $\vec{y}_2=(y_{k+1}, y_{k+2} \ldots y_K)^T$ are MD vectors, and K=M+k and K>k. Suppose that $f(\vec{x}_1, \vec{x}_2)=g(\vec{y}_1, \vec{y}_2)$ mathematically. Because the transformation between the $\{\vec{x}_1, \vec{x}_2\}$ and $\{\vec{y}_1, \vec{y}_2\}$ spaces can be generally non-linear, uniform samples of $g(\vec{y}_1, \vec{y}_2)$ in the $\{\vec{y}_1, \vec{y}_2\}$ space produce generally nonuniform samples of $f(\vec{x}_1, \vec{x}_2)$ in the $\{\vec{x}_1, \vec{x}_2\}$ space. The MDI task is to estimate uniform samples of $f(\vec{x}_1, \vec{x}_2)$ in the $\{\vec{x}_1, \vec{x}_2\}$ space from a set of measured uniform samples of $g(\vec{y}_1, \vec{y}_2)$ in the $\{\vec{y}_1, \vec{y}_2\}$ space, where the sampling rate satisfies the Nyquist conditions. In a wide class of MDI problems such as those that arise in medical imaging, the transformation between the $\{\vec{x}_1, \vec{x}_2\}$ and $\{\vec{y}_1, \vec{y}_2\}$ spaces has a general form, given by $$\vec{x}_1 = \vec{h}_1(\vec{y}_1) \quad (1a)$$

$$\vec{x}_2 = \vec{h}_2(\vec{y}_1, \vec{y}_2) = a\vec{y}_2 + \vec{b}(\vec{y}_1), \quad (1b)$$

where $\vec{h}_2$ denotes a general linear transformation (LT) between the $\{\vec{x}_2\}$ and $\{\vec{y}_2\}$ subspaces, whereas $\vec{h}_1$ denotes a general non-LT between the $\{\vec{x}_1\}$ and $\{\vec{y}_1\}$ subspaces. The known matrix a is independent of $\vec{y}_1$ and $\vec{y}_2$, and the known vector $\vec{b}$ can be any real or complex function of $\vec{y}_1$. The known matrix a and vector $\vec{b}$ represent transfer functions (i.e., a set of relationships) which relate the first set of samples $f(\vec{x}_1, \vec{x}_2)$ to the second set of samples $g(\vec{y}_1, \vec{y}_2)$ (i.e., the two sampling spaces) in a known manner.

Let $F(\vec{x}_1, \vec{v}_{\vec{x}2})$ and $G(\vec{y}_1, \vec{v}_{\vec{y}2})$ be the partial FTs of $f(\vec{x}_1, \vec{x}_2)$ and $g(\vec{y}_1, \vec{y}_2)$ with respect to $\vec{x}_2$ and $\vec{y}_2$, respectively, where $\vec{v}_{\vec{x}2}$ and $\vec{v}_{\vec{y}2}$ denote the corresponding frequencies of $\vec{x}_2$ and $\vec{y}_2$. It can be shown that $$F(\vec{x}_1, \vec{v}_{\vec{x}2}) = \|a\| G(\vec{y}_1, a^T \vec{v}_{\vec{x}2}) e^{-j2\pi \vec{v}_{\vec{x}2} \cdot \vec{b}(\vec{y}_1)}, \quad (2)$$

where $\|a\|$ and $a^T$ are the determinant and transpose of a. Because $G(\vec{y}_1, \vec{v}_{\vec{y}2})$ can readily be obtained with the fast FT (FFT) 104 from the measured samples of $g(\vec{y}_1, \vec{y}_2)$ in $\{\vec{y}_2\}$ subspace, one can calculate $F(\vec{x}_1, \vec{v}_{\vec{x}2})$ 106 by using Eqn. (2) and then $f(\vec{x}_1, \vec{x}_2)$ in the $\{\vec{x}_2\}$ subspace by invoking the inverse FFT 108. Therefore, the CPU 14 accomplishes the interpolation task in the $\{\vec{x}_2\}$ subspace and effectively reduces the original KD interpolation task of Eqn. (1) to a kD one between the $\{\vec{x}_1\}$ and $\{\vec{y}_1\}$ subspaces.

For another class of MDI problems, the transformation between the $\{\vec{x}_1\}$ and $\{\vec{y}_1\}$ subspaces is described by Eqn. (1a), whereas the transformation between the $\{\vec{x}_2\}$ and $\{\vec{y}_2\}$ subspaces is given by $$x_{k+i} = c_i y_{k+i} + b_i(\vec{y}_1, y_{k+1}, y_{k+2} \ldots y_{k+i-1}), \quad (3)$$

where $x_{k+i}$, $y_{k+i}$, $b_i$ and $c_i$ are the components of $\vec{x}_2$, $\vec{y}_2$, $\vec{b}$ and $\vec{c}$, i=1, 2 ... M. We assume that the vectors $\vec{b}$ and $\vec{c}$ are known. It should be noted that $\vec{b}$ in Eqn. (1b) is completely independent of $\vec{y}_2$, whereas $\vec{b}$ in Eqn. (3) can be a general non-linear function of the components of $\vec{y}_2$. One can show that $F(\vec{x}_1, \vec{v}_{\vec{x}2})$ can be expressed as $$F(\vec{x}_1, v_{k+1}, v_{k+2} \ldots v_{k+M}) = c_1 e^{-j2\pi v_{k+1} b_1(\vec{y}_1)} \times \quad (4)$$
$$\int d y_{k+1} e^{-j2\pi c_1 v_{k+1} y_{k+1}} G^{(M-1)}(\vec{y}_1, y_{k+1}, v_{k+2} \ldots v_{k+M})$$

where $\vec{v}_{\vec{x}2} = (v_{k+1}, v_{k+2} \ldots v_{k+M})^T$, and $$G^{(i)}(\vec{y}_1, y_{k+1} \ldots y_{k+M-i}, v_{k+M-i+1} \ldots v_{k+M}) = \quad (5)$$
$$c_{M-i+1} e^{-j2\pi v_{k+M-i+1} b_{M+1-i}(\vec{y}_1, y_{k+1} \ldots y_{k+M-i})} \times$$
$$\int d y_{k+M-i+1} e^{-j2\pi c_{M-i+1} v_{k+M-i+1} y_{k+M-i+1}}$$
$$G^{(i-1)}(\vec{y}_1, y_{k+1} \ldots y_{k+M-i}, y_{k+M-i+1}, v_{k+M-i+2} \ldots v_{k+M})$$

with $G^{(0)}(\vec{y}_1, y_{k+1} \ldots y_{k+M}) = g(\vec{y}_1, \vec{y}_2)$ and i=1, 2 ... M-1. The integrals in Eqns. (4) and (5) denote 1D FTs that can be calculated by invoking the 1D FFT. Using Eqns. (4) and (5), the CPU 14 can calculate $F((\vec{x}_1, \vec{v}_{\vec{x}2})$ from knowledge of $g(\vec{y}_1, \vec{y}_2)$ in the $\{\vec{y}_2\}$ subspace. From $F((\vec{x}_1, \vec{v}_{\vec{x}2})$, the CPU 14 can obtain $f(\vec{x}_1, \vec{x}_2)$ by invoking the inverse FFT and thus accomplish the interpolation task in the $\{\vec{x}_2\}$ subspace. Therefore, the original KD interpolation task of Eqns. (1a) and (3) is thus reduced effectively to a kD one between the $\{\vec{x}_1\}$ and $\{\vec{y}_1\}$ subspaces.

Figure 3B:
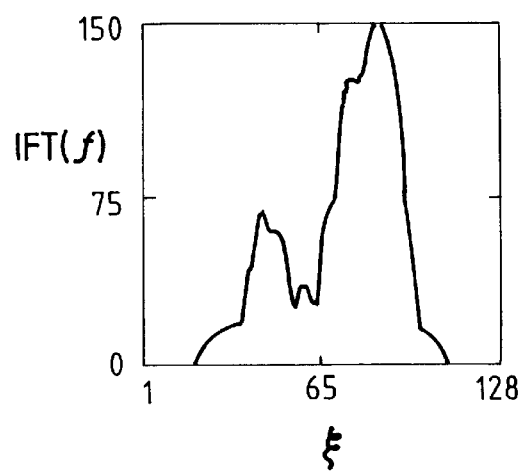

In 2D SPECT, which is a nuclear medicine imaging modality, the CPU 14 can measure uniform samples of $g(v_m, \phi)$ in the $\{v_m, \phi\}$ space using the sampling device 12. Reconstruction of a SPECT image requires uniform samples of $f(v_a, \phi_0)$ in the $\{v_a, \phi_0\}$ space. When constant attenuation is considered in 2D SPECT, one can show that $f(v_a, \phi_0) = g(v_m, \phi)$, provided $$v_a = \sqrt{v_m^2 - v_\mu^2} \quad (6a)$$

$$\phi_0 = \phi - \tan^{-1}\left(j\frac{v_\mu}{v_m}\right) \quad (6b)$$

where $v_\mu$ is a known constant. It appears that a 2D interpolation may be used to calculate uniform samples of $f(v_a, \phi_0)$ in the $\{v_a, \phi_0\}$ space from that of $g(v_m, \phi)$ in the $\{v_m, \phi\}$ space. However, comparison of Eqns. (6b) and (1b) indicates that $\phi_0$ is a 1D LT of $\phi$ with a=1 and $$b = -\tan^{-1}\left(j\frac{v_\mu}{v_m}\right)$$

and that the interpolation between the $\{\phi_0\}$ and $\{\phi\}$ subspaces can thus be accomplished by using Eqn. (2). Thus the seemingly 2D interpolation task here effectively becomes a 1D interpolation between task between the $\{v_a\}$ and $\{v_m\}$ subspaces. In fact, this is probably the only practically viable approach to accomplishing the task of estimating $f(v_a, \phi_0)$ from knowledge of $g(v_m, \phi)$ because it involves a complex transformation between the $\{\phi_0\}$ and $\{\phi\}$ subspaces. We generated two sets of uniform samples of $g(v_m, \phi)$ on a 128×128 and a 128×16 grid, respectively, in the $\{v_m, \phi\}$ space, simulating the measurements in SPECT. Using our approach, the CPU 14 calculated uniform samples of $f(v_a, $ $\phi_0$) in $\{v_a, \phi_0\}$ from the two sets of simulated data. For the purpose of clearly showing the accuracy of the obtained results, we display in FIG. 3 the inverse FT (IFT) of the interpolated $f(v_a, \phi_0)$ with respect to $v_a$ (instead of the interpolated $f(v_a, \phi_0)$ itself). These results clearly demonstrate that our approach can yield accurate results even if the samples of $g(v_m, \phi)$ in the $\{\phi\}$ subspace are sparse (see FIG. 3b).

In fan-beam CT, one can measure uniform samples of $g(t, \phi)$ in the $\{t, \phi\}$ space. Reconstruction of a CT image requires uniform samples of $f(\xi, \phi_0)$ in the $\{\xi, \phi_0\}$ space. One can show that $f(\xi, \phi_0) = g(t, \phi)$, provided $$\xi = t \frac{D}{\sqrt{D^2 + t^2}} \tag{7a}$$

$$\phi_0 = \phi + \tan^{-1}\left(\frac{t}{D}\right), \tag{7b}$$

where D is a known constant. Because the transformation in Eqn. (7) is non-linear, a 2D interpolation may be used to calculate uniform samples of $f(\xi, \phi_0)$ in the $\{\xi, \phi_0\}$ space from that of $g(t, \phi)$ in the $\{t, \phi\}$ space. However, comparison of Eqns. (7b) and (1b) indicates that $\phi_0$ is a 1D LT of $\phi$ with a=1 and $$b = \tan^{-1}\left(\frac{t}{D}\right)$$

and that the interpolation between the $\{\phi_0\}$ and $\{\phi\}$ subspaces can thus be accomplished by using Eqn. (2). Hence, the 2D interpolation task in 2D fan-beam CT is reduced effectively to a 1D interpolation task between the $\{\xi\}$ and $\{t\}$ subspaces.

Figure 4A:
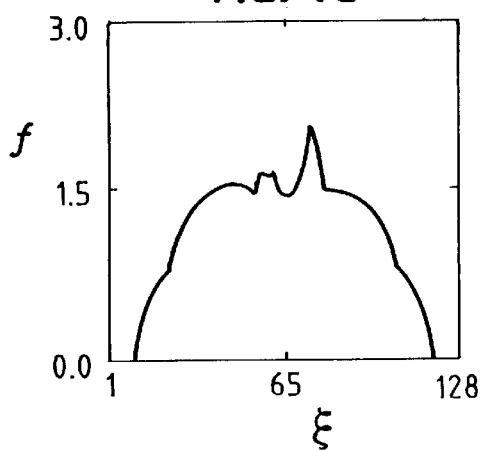
FIG. 4 depicts results of data interpolated on a 128×128 grid at two different values of $\phi_0$.
Figure 4B:
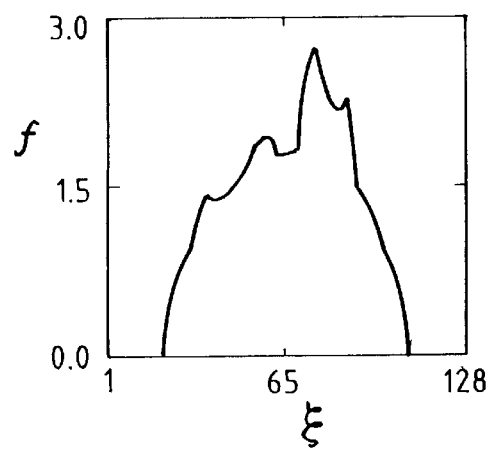
Figure 5A:
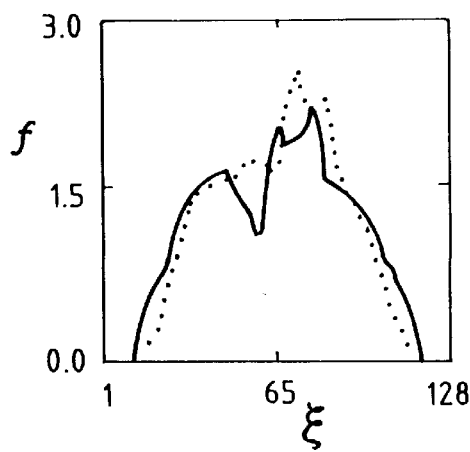
FIG. 5 also depicts results of data interpolated on a 128×128 grid at two different values of $\phi_0$.
Figure 5B:
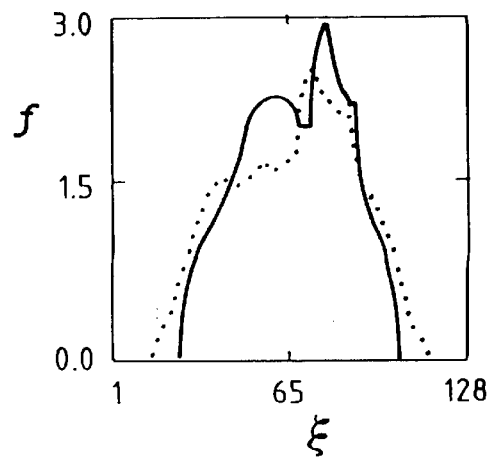

We generated two sets of uniform samples of $g(t, \phi)$ on 128×128 and 128×16 grids, respectively, in the $\{t, \phi\}$ space, simulating the measurements in CT. Applying our approach and the frequently used bilinear interpolation (BI) technique, we calculated uniform samples of $f(\xi, \phi_0)$ in $\{\xi, \phi_0\}$ from the two sets of the computer-simulated data. The data set used in FIG. 4 contains 128 grids in the $\{\phi\}$ subspace. In this situation, the results obtained with our approach coincide with the true values, suggesting that our approach can generate accurate values of $f(\xi, \phi_0)$. However, as shown in FIG. 4, despite the fact that the BI technique can yield reasonably accurate results, discrepancies between the BI results and the true values are evident. For the data set that contains only 16 grids in the $\{\phi\}$ subspace, as shown in FIG. 5, the BI technique performs poorly, whereas our approach still yields reasonably accurate results. For the above numerical experiments, our approach is about 3 times faster than the BU technique. Quantitative evaluation indicates that, in terms of root-mean-square error, our approach is generally 5 times more accurate than the BI technique.

In 2D diffraction tomography (DT) with plane incident wave, one can measure uniform samples of $g(v_m, \phi)$ in the $\{v_m, \phi\}$ space. Reconstruction of a DT image requires uniform samples of $f(v_a, \phi_0)$ in the $\{v_a, \phi_0\}$ space. One can show that $f(v_a, \phi_0) = g(v_m, \phi)$, provided $$v_a = \sqrt{v_m^2 + \left(\sqrt{v_0^2 - v_m^2} - v_0^2\right)} \tag{8a}$$

-continued $$\phi_0 = \phi + \tan^{-1}\left(\frac{\sqrt{v_0^2 - v_m^2} - v_0}{v_m}\right), \tag{8b}$$

where $v_0$ is a known constant and $|v_m| \leq v_0$. Because the transformation in Eqn. (8) is non-linear, a 2D interpolation may be used to calculate uniform samples of $f(v_a, \phi_0)$ in the $\{v_a, \phi_0\}$ space from that of $g(v_m, \phi)$ in the $\{v_m, \phi\}$ space. However, comparison of Eqns. (8b) and (1b) indicates that $\phi_0$ is a 1D LT of $\phi$ with a=1 and $$b = \tan^{-1}\left(\frac{\sqrt{v_0^2 - v_m^2} - v_0}{v_m}\right)$$

and that the interpolation between the $\{\phi_0\}$ and $\{\phi\}$ subspaces can thus be accomplished by using Eqn. (2). Hence, the 2D interpolation task in DT is reduced effectively to a 1D interpolation task between the $\{v_a\}$ and $\{v_m\}$ subspaces.

In spiral CT, one can measure uniform samples of $g(t, \phi, z')$ in the $\{t, \phi, z'\}$ space. However, image reconstruction in spiral CT requires uniform samples of $f(\xi, \phi_0, z)$ in the $\{\xi, \phi_0, z\}$ space. One can show that $f(\xi, \phi_0, z) = g(t, \phi, z')$, provided $$\xi = t \frac{D}{\sqrt{D^2 + t^2}} \tag{9a}$$

$$\phi_0 = \phi + \tan^{-1}\left(\frac{t}{D}\right) \tag{9b}$$

$$z = z' + \beta(\phi), \tag{9c}$$

where $\beta(\phi)$ is a known function of $\phi$, and its form depends upon how the scanning is performed in a spiral CT experiment. Because the transformation in Eqn. (9) is obviously non-linear, a 3D interpolation may be used to calculate uniform samples of $f(\xi, \phi_0, z)$ in the $\{\xi, \phi_0, z\}$ space from that of $g(t, \phi, z')$ in the $\{t, \phi, z'\}$ space. However, one can show that the transformation between the $\{\phi_0, z\}$ and $\{\phi, z'\}$ subspaces in Eqns. (9b) and (9c) satisfies Eqn. (3) with $c_1 = c_2 = 1$, $$b_1 = \tan^{-1}\left(\frac{t}{D}\right)$$

and $b_2 = \beta(\phi)$ and that the interpolation between the two subspaces can thus be accomplished by using Eqns. (3) and (4). Therefore, the 3D interpolation task in spiral CT is reduced effectively to a 1D interpolation task between the $\{\xi\}$ and $\{t\}$ subspaces.

A method and apparatus are provided that can reduce the computational burden by reducing interpolation dimensions in two general classes of MDI problems in Eqns. (1) and (3). This approach is as accurate as the multi-dimensional interpolation techniques that are based upon the WST but is inherently more efficient than the latter because it utilizes the FFT technique. Because the WST interpolation techniques are, in general, more accurate than the linear interpolation (LI) technique, our approach is generally more accurate than the multidimensional LI technique. Our numerical studies in 2D interpolation problems demonstrate that the proposed approach is more accurate and even (about 3 times) faster than the most commonly used BI technique. The reduction in computation time is expected to be greater as the number of interpolation dimensions increases. Furthermore, our approach can accomplish some interpolation tasks where other interpolation techniques may not be applicable. (See the example for 2d SPECT.) The proposed approach can also be applied to other MDI problems such as MRI and PET in medical imaging. Although we have illustrated our approach to MDI problems using examples from medical imaging, we expect that it can find applications in other engineering and scientific fields.

A specific embodiment of a method and apparatus for constructing a multidimensional interpolator according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

I claim:

1. A method of interpolating a first set of multidimensional sample values from a second set of multidimensional sample values, such method comprising the steps of:
   determining a set of relationships between a second sampling space from which the second set of samples are obtained and a first sampling space into which the first set of samples are interpolated;
   calculating a partial Fourier transform of the second set of samples;
   obtaining a partial Fourier transform of the first set of samples using the calculated partial Fourier transform of the second set of samples based upon the determined relationship between the first and second space; and
   performing an inverse partial Fourier transform on the obtained partial Fourier transform of the first set of sample values to recover the first set of sample values.

2. The method of interpolating as in claim 1 further comprises defining the first and set of samples by functions, $f(\vec{x}_1, \vec{x}_2)$, and $g(\vec{y}_1, \vec{y}_2)$ respectively, where each function is a K dimensional band-limited function, where $\vec{x}_1=(x_1, x_2, \ldots x_k)^T$ and $\vec{y}_1=(y_1, y_2, \ldots y_k)^T$ are k dimensional vectors, $\vec{x}_2=(x_{k+1}, x_{k+2}, \ldots x_K)^T$ and $\vec{y}_2=(y_{k+1}, y_{k+2}, \ldots y_K)^T$ are M dimensional vectors, and where K=M+k and K>k.

3. The method of interpolating as in claim 1 further comprising collecting the second set of samples under a fan-beam sampling format.

4. The method of interpolating as in claim 3 further comprising defining a format of the first set of samples as being parallel ray.

5. The method of interpolating as in claim 4 further comprising the step of determining a one-to-one relationship between the first and second sampling space where the first set of samples are interpolated under a parallel-ray format and the second set of samples are obtained under fan-beam format.

6. The method of interpolating as in claim 1 further comprising collecting the second set of samples using a spiral CT sampling format.

7. The method of interpolating as in claim 6 further comprising defining the second sampling format as being parallel ray.

8. The method of interpolating as in claim 7 further comprising the step of determining a one-to-one relationship between the first and second sampling space where the first set of samples are interpolated under the parallel-ray format and the second set of samples are obtained using the spiral CT format.

9. Apparatus for interpolating a first set of multidimensional sample values from a second set of multidimensional sample values, such apparatus comprising:
   means for determining a set of relationships between a second sampling space from which the second set of samples are obtained and a first sampling space into which the first set of samples are interpolated;
   means for calculating a partial Fourier transform of the second set of samples;
   means for obtaining a partial Fourier transform of the first set of samples using the calculated partial Fourier transform of the second set of samples based upon the determined relationship between the first and second space; and
   means for performing an inverse partial Fourier transform on the obtained partial Fourier transform of the first set of sample values to recover the first set of sample values.

10. The apparatus for interpolating as in claim 9 wherein the first and second set of samples further comprise functions, $f(\vec{x}_1, \vec{x}_2)$, and $g(\vec{y}_1, \vec{y}_2)$.

11. The apparatus for interpolating as in claim 10 wherein the functions, $f(\vec{x}_1, \vec{x}_2)$, and $g(\vec{y}_1, \vec{y}_2)$ further comprise K dimensional band-limited functions, where $\vec{x}_1=(x_1, x_2, \ldots x_k)^T$ and $\vec{y}_1=(y_1, y_2, \ldots y_k)^T$ are k dimensional vectors, $\vec{x}_2=(x_{k+1}, x_{k+2}, \ldots x_K)^T$ and $\vec{y}_2=(y_{k+1}, y_{k+2}, \ldots y_K)^T$ are M dimensional vectors, and where K=M+k and K>k.

12. The apparatus for interpolating as in claim 9 further comprising means for collecting the second set of samples under a fan-beam sampling format.

13. The apparatus for interpolating as in claim 12 wherein the first sampling space further comprising a parallel ray format.

14. The apparatus for interpolating as in claim 9 further comprising means for collecting the second set of samples using a spiral CT sampling format.

15. The apparatus for interpolating as in claim 14 wherein the first sampling space further comprises a parallel ray format.

16. Apparatus for interpolating a first set of multidimensional sample values from a second set of multidimensional sample values, such apparatus comprising:
   a sampling space processor which determines a set of relationships between a second sampling space from which the second set of samples are obtained and a first sampling space into which the first set of samples are interpolated;
   a Fourier processor adapted to calculating a partial Fourier transform of the second set of samples;
   a matrix processor adapted to obtain a partial Fourier transform of the first set of samples using the calculated partial Fourier transform of the second set of samples based upon the determined relationship between the first and second space; and
   a solution processor adapted to perform an inverse partial Fourier transform on the obtained partial Fourier transform of the first set of sample values to recover the first set of sample values.

17. The apparatus for interpolating as in claim 16 wherein the first and second set of samples further comprise functions, $f(\vec{x}_1, \vec{x}_2)$, and $g(\vec{y}_1, \vec{y}_2)$.

18. The apparatus for interpolating as in claim 17 wherein the functions, $f(\vec{x}_1, \vec{x}_2)$, and $g(\vec{y}_1, \vec{y}_2)$ further comprise K dimensional band-limited functions, where $\vec{x}_1=(x_1, x_2, \ldots x_k)^T$ and $\vec{y}_1=(y_1, y_2, \ldots y_k)^T$ are k dimensional vectors, $\vec{x}_2=(x_{k+1}, x_{k+2}, \ldots x_K)^T$ and $\vec{y}_2=(y_{k+1}, y_{k+2}, \ldots y_K)^T$ are M dimensional vectors, and where K=M+k and K>k.

19. The apparatus for interpolating as in claim 16 further comprising a sampling array adapted to collect the second set of samples under a fan-beam sampling format.

20. The apparatus for interpolating as in claim 16 wherein the first sampling space further comprising a parallel ray format.

21. The apparatus for interpolating as in claim 16 further comprising a spiral CT sample collector adapted to collect the second set of samples using a spiral CT sampling format.

22. The apparatus for interpolating as in claim 21 wherein the first sampling space further comprises a parallel ray format.

23. A method of interpolating a first set of sample values, $f(\vec{x}_1, \vec{x}_2)$, for display on an imaging system from a second set of sample values $g(\vec{y}_1, \vec{y}_2)$ such method comprising the steps of:

determining a matrix, a, describing a set of relationships between a second sampling space from which the second set of samples are obtained and a first sampling space into which the first sampling values are interpolated;

obtaining a partial Fourier transform, $G(\vec{y}_1, \vec{v}_{y_2})$, of the second set of samples;

solving for a partial Fourier transform, $F(\vec{x}_1, \vec{v}_{\vec{x}_2})$ of the first set of samples, using the equation $$F(\vec{x}_1, \vec{v}_{\vec{x}_2}) = \|a\| G(\vec{y}_1, a^T \vec{v}_{\vec{x}_2}) e^{-j2\pi \vec{v}_{\vec{x}_2} \cdot \vec{b}(\vec{y}_1)},$$

where $\|a\|$ and $a^T$ are the determinate and transpose of a, respectively; and performing an inverse Fourier transform on $F(\vec{x}_1, \vec{v}_{\vec{x}_2})$ to recover the first set of sample values.

24. A method of interpolating a first set of sample values, $f(\vec{x}_1, \vec{x}_2)$, for display on an imaging system from a second set of sample values $g(\vec{y}_1, \vec{y}_2)$, such method comprising the steps of:

determining a matrix, a, describing a set of relationships between a second sampling space from which the second set of samples are obtained and a first sampling space into which the first sampling values are interpolated;

obtaining a partial Fourier transform, $G(\vec{y}_1, \vec{v}_{y_2})$, of the second set of samples;

solving for a partial Fourier transform, $F(\vec{x}_1, \vec{v}_{\vec{x}_2})$ of the first set of samples, using the equations $$F(\vec{x}_1, v_{k+1}, v_{k+2} \ldots v_{k+M}) = c_1 e^{-j2\pi v_{k+1} b_1(\vec{y}_1)} \times$$

$$\int dy_{k+1} e^{-j2\pi c_1 v_{k+1} y_{k+1}} G^{(M-1)}(\vec{y}_1, y_{k+1}, v_{k+2} \ldots v_{k+M}) \text{ and}$$

$$G^{(i)}(\vec{y}_1, y_{k+1} \ldots y_{k+M-i}, v_{k+M-i+1} \ldots v_{k+M}) =$$

$$c_{M-i+1} e^{-j2\pi v_{k+M-i+1} b_{M+1-i}(\vec{y}_1, y_{k+1} \ldots y_{k+M-i})} \times$$

$$\int dy_{k+M-i+1} e^{-j2\pi c_{M-i+1} v_{k+M-i+1} y_{k+M-i+1}}$$

$$G^{(i-1)}(\vec{y}_1, y_{k+1} \ldots y_{k+M-i}, y_{k+M-i+1}, v_{k+M-i+2} \ldots v_{k+M}); \text{ and}$$

performing an inverse Fourier transform on $F(\vec{x}_1, \vec{v}_{\vec{x}_2})$ to recover the first set of sample values.

* * * * *